United States Patent
Thalmann

[19]

[11] Patent Number: 6,131,452
[45] Date of Patent: *Oct. 17, 2000

[54] PROCESS AND DEVICE FOR DETECTING STRUCTURAL FAULTS OF MOVING FLAT TEXTILE MATERIALS

[75] Inventor: Markus Thalmann, Emmen, Switzerland

[73] Assignee: Rhodia Filtec AG, Emmenbruecke, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/740,362

[22] Filed: Oct. 28, 1996

Related U.S. Application Data

[63] Continuation of application No. PCT/CH96/00058, Sep. 6, 1996.

[30] Foreign Application Priority Data

Feb. 28, 1995 [CH] Switzerland .................. 558/95

[51] Int. Cl.[7] ............................... G01H 17/00
[52] U.S. Cl. ................. 73/159; 73/862.59; 26/70
[58] Field of Search .................. 73/159, 160, 37.7, 73/651, 661, 862.41, 862.59, 862.626, 862.632, 862.634; 340/675; 356/238, 429, 430, 431; 250/548, 559.01, 559.42, 559.43, 559.45, 559.48; 26/51, 51.3, 51.4, 51.5, 70

[56] References Cited

U.S. PATENT DOCUMENTS

| | | | |
|---|---|---|---|
| 2,612,677 | 10/1952 | Boley | 73/159 |
| 2,834,206 | 5/1958 | Mindheim et al. | 73/159 |
| 3,037,381 | 6/1962 | Grant et al. | 73/159 |
| 3,164,015 | 1/1965 | Schäfer | 73/159 |
| 3,357,241 | 12/1967 | King, III | 73/159 |
| 3,403,447 | 10/1968 | Taylor, Jr. | 73/159 |
| 4,189,841 | 2/1980 | Loepfe | 73/160 |
| 4,864,853 | 9/1989 | Grunder et al. | 73/160 |

FOREIGN PATENT DOCUMENTS 0 562 268 A1  9/1993  European Pat. Off. .

OTHER PUBLICATIONS

Derwent abstract of EPA 0 562 268 A1, AN 93–304726, 1997.

Primary Examiner—Hezron Williams
Assistant Examiner—Rose M. Miller
Attorney, Agent, or Firm—Michael J. Striker

[57] ABSTRACT

The device for on-line detection of structural faults in moving flat textile materials includes a spade-like leaf spring contact sensor (2) having a length of from 5 to 20 cm which is advantageously rounded and/or chamfered for engagement with threads in the flat textile materials; a mounting device (5) for mounting the spade-like leaf spring contact sensor (2) so that the contact sensor is at a positioning angle of 10 to 60° relative to the textile material, the contact sensor (2) is oriented perpendicular to a thread direction and a free end of the contact sensor (2) is urged into engagement with the threads in the flat textile material, whereby the contact sensor (2) experiences regular deflections due to the thread pattern and irregular deflections due to structural faults in the thread pattern as the moving textile material moves past the contact sensor (2); and a vibration pickup (4) for measuring the regular and the irregular deflections of the contact sensor to form a sensor motion measurement signal for subsequent analysis and signaling of the structural faults.

11 Claims, 2 Drawing Sheets

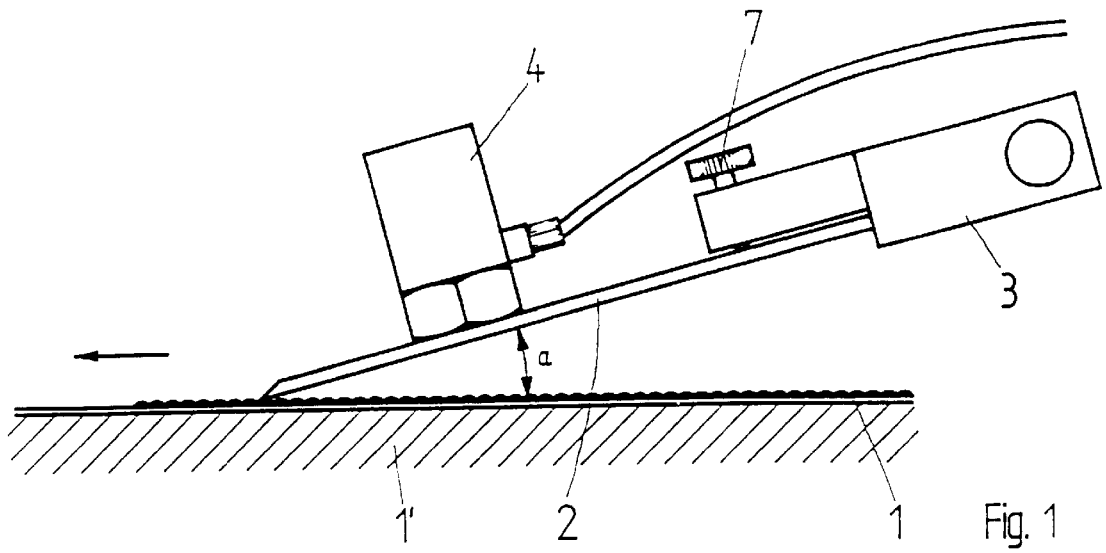
Fig. 1
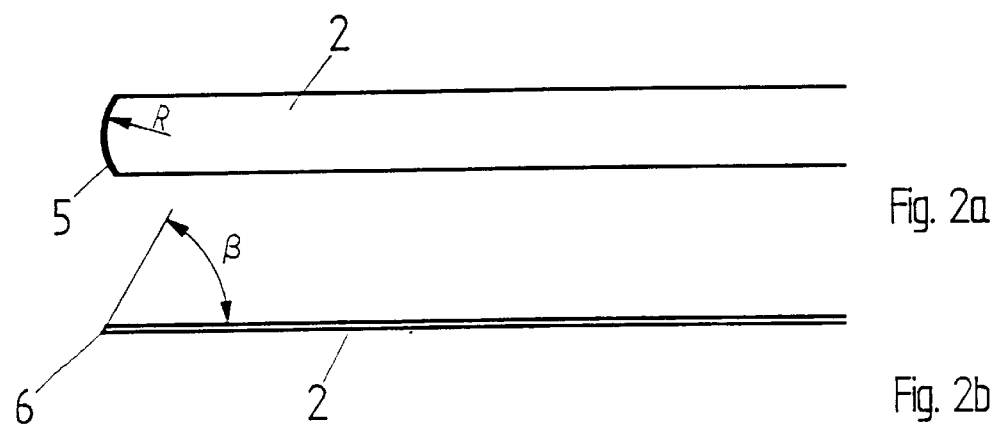
Fig. 2a
Fig. 2b
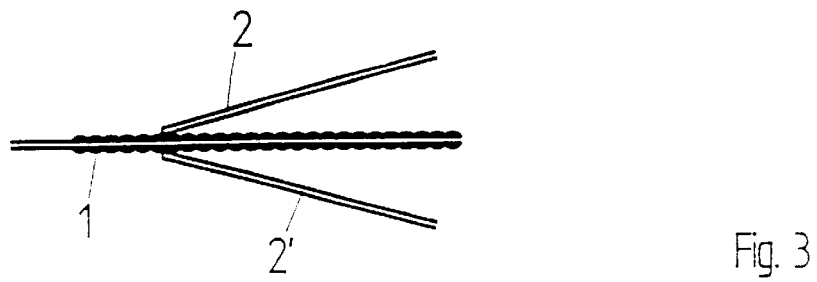
Fig. 3

PROCESS AND DEVICE FOR DETECTING STRUCTURAL FAULTS OF MOVING FLAT TEXTILE MATERIALS

This application was originally filed on Sep. 6, 1996 as PCT International Application number PCT/CH96/00058 and is therefore considered to be a continuation of PCT International Application number PCT/CH96/00058.

BACKGROUND OF THE INVENTION

The invention relates to a process for on-line detection of structural faults of moving flat textile materials by means of a rigidly fastened contact sensor, and to a device for performing the process.

As a rule, ascertaining visible structural faults in flat textile materials is done by optical methods. For instance, European Patent Disclosure EP-A 0 562 268 discloses an apparatus that investigates cloth containing warp threads for thread errors using a lighting device that passes at a certain angle relative to the warp threads and is equipped with a light-sensitive element that sends its signals onto an electronic evaluation unit. Where the faults are visually not so clearly defined, the testing method no longer functions.

SUMMARY OF THE INVENTION

The object of the invention is to create a process that makes it possible for structural faults located crosswise to the direction of motion of the fabric being moved forward and that affect the entire width thereof, to be determined quickly or in other words to be recognized, detected, and directly evaluated.

Another object is to furnish a measuring device that measures the structural faults detected and at the same time evaluates them.

This object is attained in accordance with the invention in that the free length of the contact sensor, of from 5 to 20 cm, forms a positioning angle $\alpha$ of 10 to 60° with the flat textile material, and the motion of the contact sensor is recorded as a measurement signal and automatically evaluated.

Since the contact sensor in the mounting, with the measured value pickup, represents a system capable of oscillation, the free length of the contact sensor, its cross section and the contact pressure, together with the mass of the measured value pickup, are of substantial significance. The system is excited by the ripple frequency that results from the structure of the fabric and the feeding speed. The natural frequency of the system should be low relative to the ripple frequency. A free length of 5 to 20 cm and in particular 10 to 20 cm has proved to be expedient. It is also expedient to provide a positioning angle $\alpha$ of 10 to 60°, in particular 10 to 45° and preferably 10 to 15°. A positioning angle $\alpha$ of less than 10° has the disadvantage that faults originating in a single weft thread cannot be detected, since the adjacent weft threads prevent the tip of the contact sensor from being lowered into an indentation; a positioning angle $\alpha$ of more than 60° produces an excessive dependency of the measurement signal on the feeding speed of the fabric.

It is expedient to perform the measurement of the motion by means of a vibration pickup. The intensity of the motion of the contact sensor in the form of a leaf spring furnishes the information about the structure of the fabric. It is advantageous that the vibration pickup can still furnish usable signals even when the structural faults are very small.

In one embodiment, it is expedient to perform the measurement of the motion by means of a traveling pickup. During the measurement, the contact sensor scans the structure of the fabric with the scanning edge of its rounded off portion, and it executes motions that correspond to the surface structure of the fabric. Since the measured value pickup scans the motion of the contact sensor in contactless fashion, considerably higher feeding speeds or finer structures to be determined are possible.

It is expedient, in another embodiment, to perform the measurement of the motion by means of an acoustical pickup. As in the case of the traveling pickup, the measurement is contactless. Higher feeding speeds can thus be used, and finer structural faults can be found. In addition, the signal is available in a form that is directly accessible to human senses and can thus be detected directly by the monitoring worker, for instance by headphones.

For performing the process, a contact sensor is provided that is embodied as a spadelike leaf spring. The term "spadelike" is intended to express the fact that the length of the leaf spring is a multiple of its width. The leaf spring, in its simplest form, comprises hardened spring band steel.

It is expedient for the leaf spring fastened by one end to be provided on its free end with a convex rounding off. The rounding off has the advantage that the leaf spring, disposed parallel to the warp thread, cannot catch on its edges as it touches the length of fabric. Another advantage is considered to be that possible twisting of the fabric in motion during the monitoring, that is, if the angle of 90° between the leaf spring and the weft thread is not maintained, does not cause any sacrifice in sensitivity.

The radius R of the rounding off amounts to from half the width of the leaf spring to 150 mm. A radius of 10 to 100 mm, and in particular 10 to 40 mm, has proved especially advantageous.

The rounded end has a chamfer. The edge that touches the cloth, or in other words the edge on the side toward the cloth, forms an acute angle $\beta$. The angle $\beta$ is defined as a function of the fineness of the structure to be measured but is also defined by the desired rigidity of the tip. The tip may also comprise an abrasionproof material, such as ceramic or corundum.

It is advantageous if the angle $\beta$ is from 30 to 90°, in particular 50 to 90° and preferably 60 to 90°. An angle smaller than 30° has the disadvantage that the edge wears down too fast and is soft; angle greater than 90°, for certain values of a positioning angle $\alpha$, could lead to sacrifices in sensitivity.

It is expedient to embody the measured value pickup as a vibration pickup. A vibration pickup has the advantage that usable signals can still be obtained even with very small structural faults.

In a variant, it is expedient to embody the measured value pickup as a traveling pickup. A traveling pickup has the advantage that scanning is done contactlessly, and thus considerably higher feeding speeds are possible or finer structures can be determined. In a further variant it is expedient to embody the measured value pickup as an acoustical pickup. An acoustical pickup has the advantage that the measurement is done contactlessly. Higher feeding speeds can therefore be used and finer structural faults can be found. In addition, the signal is available in a form that is directly accessible to human senses and can thus be detected directly by the monitoring worker.

The leaf spring also, however, furnishes information about the magnitude and intensity of the motion across the fabric structure. The structural measurement can thus be reduced, in a first variant, to a displacement measurement.

To that end, the measured value pickup in the form of a spacing or distance-measuring sensor is secured in such a way to the rigid part of the mounting in the region of the end of the leaf spring that the end of the contact sensor moves in the region of the distance-measuring sensor. Commercially available optical, magnetic, inductive or capacitive pickups can be considered for the distance-measuring sensors here.

BRIEF DESCRIPTION OF THE DRAWING

The objects, features and advantages of the invention will now be illustrated in more detail with the aid of the following description of the preferred embodiments, with reference to the accompanying figures in which:

FIG. 1 is a side view of a device according to the invention;

FIG. 2a is a plan view of a contact sensor from a device according to the invention;

FIG. 2b is a cross-sectional view through the contact sensor shown in FIG. 3;

FIG. 3 is a cutaway side view of another embodiment of the device according to the invention with two contact sensors.

FIG. 1, shows a moving flat textile material in the form of a length of fabric to be checked under reference number 1. The travel direction is represented by an arrow. The length of fabric 1 rests flat on a fixed bearing surface 1'. The bearing surface 1' for instance comprises a glass slab at least 5 mm thick. A measuring head, in its essential parts, comprises a contact sensor 2, a mounting 3, and a measured value pickup 4. Only when it takes the form of a vibration pickup is the measured value pickup 4 connected directly to the contact sensor 2. In the variants of the measured value pickup 4 where it is a traveling pickup or acoustical pickup, the pickups are expediently disposed above the contact sensor 2. An adjusting screw 7 is integrated with the mounting 3. The contact sensor 2 forms an angle α with the moving length of fabric.

In FIG. 2a, the contact sensor 2 is shown embodied as a leaf spring. At its tip, the contact sensor 2 has a convex rounding off 5 having a radius R.

In FIG. 2b, the chamfer 6 of the tip of the contact sensor 2, with an angle β, can be seen.

FIG. 3 shows a moving length of fabric, which is provided with the contact sensor 2 from an upper side and with a second contact sensor 2' from its lower side. This arrangement has the advantage that the useful signal can be twice as great as in the version with one measurement head. To that end, the signals of the two pickups must be added together with correct phases. The phase relationship is determined by the longitudinal offset of the two scanning edges from one another, which in turn depends on the structural size (weft thread titer) of the cloth.

FIG. 4 shows the diagram for signal evaluation. The measurement signal of the sensor 4, which measures the motion of the contact sensor 2, is further processed in an amplifier 22. The signal obtained is recorded directly on paper in a known manner with a fast plotter 23. The regular, flawless structure of the flat textile material causes a deflection for every weft thread and thus produces an evenly wide band on the plotter. The flaws are immediately apparent as excessive signals as compared with the regular signal. For additional visual control, an oscilloscope 24 can be furnished.

Figure 4:
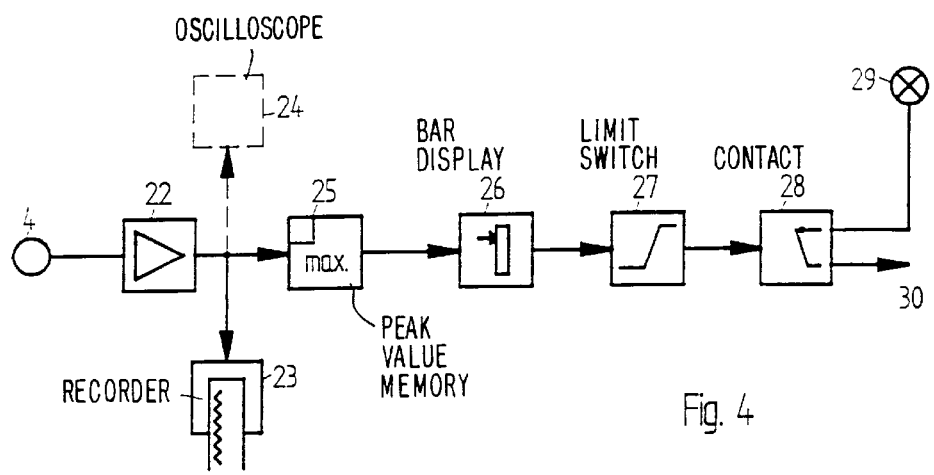
FIG. 4 is a block diagram of a device for amplitude signal evaluation of a measurement signal from a device according to the invention.

For further processing, the measurement signal is supplied to a peak value memory 25. The peak value memory 25 stores the very brief error signal as needed, if it originates in only one affected thread. The stored peak value is rendered visible on a bar display 26, for instance. By means of an adjustable limit value switch 27, an alarm signal can be obtained via a contact 28; by means of an alarm light 29, for instance, this draws the attention of the operating worker or turns off a machine 30 by remote control.

Figure 5:
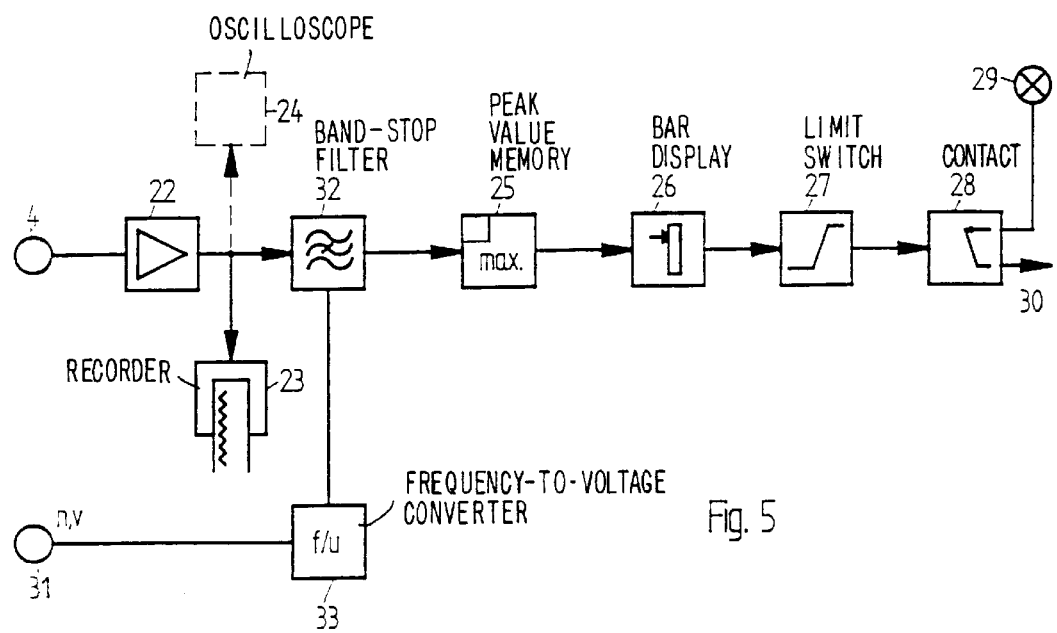
FIG. 5 is a block diagram of a device for frequency signal evaluation of a measurement signal from a device according to the invention.

In FIG. 5, the signal evaluation that takes a variable fabric feeding speed into account is shown. The frequency of the measurement signal is the product of the feeding speed and the thread density.

$$f_{regular} = V_{feeding} \times \text{weft thread density}$$

Weft thread density means the number of weft threads per unit of length.

If irregularities are found, caused by structural flaws in the cloth, then this can be seen from the increase in different-frequency components of the signal. In order to detect only these interfering frequencies, the regular frequency $f_{regular}$ is filtered out by a controllable band-stop filter 32. The control signal is obtained from the sensor 31, which measures the feeding speed, by means of a frequency-to-voltage converter 33. A structural fault generates an output signal at the band-stop filter 32, which is evaluated analogously to the description of FIG. 4.

In operation, the mounting 3 assures that the contact sensor 2 will scan the moving fabric with the correct positioning angle α and the optimal contact pressure. The contact pressure, fastening length, sensor weight and speed of the length of fabric must be adapted to one another. The contact pressure can be freely adjusted without having to shift the mounting 3 by means of the adjusting screw 7.

I claim:

1. A process for on-line detection of structural faults in moving flat textile materials by means of a fixed spade-shaped leaf spring contact sensor, said process comprising the steps of:

a) providing a spade-shaped leaf spring contact sensor (2) having a length of from 5 to 20 cm and a free end and providing a vibration pickup (4) for measuring motions of the spade-shaped leaf spring contact sensor (2);

b) urging said free end of the spade-shaped leaf spring contact sensor (2) into engagement with a portion of a flat textile material (1) including threads arranged next to each other and extending in a thread direction;

c) orienting said spade-shaped leaf spring contact sensor at a positioning angle α of from 10 to 60° to said portion of the flat textile material (1);

d) moving said portion of said flat textile material (1) including said threads relative to said spade-shaped leaf spring contact sensor during the urging and the orienting of steps b) and c) to cause motions of said space-shaped leaf spring contact sensor including regular deflections of said spade-shaped leaf spring contact sensor due to said threads and irregular deflections of the spade-shaped leaf spring contact sensor due to the structural faults of the textile material;

e) continuously measuring said motions of the spade-shaped leaf spring contact sensor (2) including the regular deflections and the irregular deflections by means of the vibration pickup (4);

e) permanently recording said motions of the spade-shaped leaf spring contact sensor (2) measured by means of the vibration pickup (4); and f) automatically analyzing the motions of the spade-shaped leaf spring contact sensor (2) measured by means of the vibration pickup (4) in order to detect the structural faults.

2. The process as defined in claim 1, wherein said threads in said flat textile material are weft threads and said thread direction is a weft thread direction, the flat textile material is moved in a textile motion direction perpendicular to said weft thread direction during the moving and said contact sensor is arranged to extend at an angle of 90° relative to said weft thread direction.

3. The process as defined in claim 1, further comprising displaying said motions of the spade-shaped leaf spring contact sensor (2) measured by means of the vibration pickup (4) by a display means comprising an oscilloscope.

4. A device for on-line detection of structural faults in moving flat textile materials, said device comprising a spade-shaped leaf spring contact sensor (2) having a length of from 5 to 20 cm and a free end;

mounting means (5) for mounting the spade-shaped leaf spring contact sensor (2) in a fixed relationship relative to a moving flat textile material having a plurality of threads arranged next to each other and oriented in a thread direction so that the contact sensor is at a positioning angle of from 10 to 60° relative to the textile material, the contact sensor (2) is oriented perpendicular to the thread direction and the free end of the contact sensor (2) is urged into engagement with said flat textile material, whereby the contact sensor (2) experiences regular deflections due to said threads and irregular deflections due to the structural faults as the moving textile material moves past the contact sensor (2); and means (4) for measuring the regular and the irregular deflections of the contact sensor to form a sensor motion measurement signal.

5. The device as defined in claim 4, further comprising means (23) for permanently recording and displaying the sensor motion measurement signal.

6. The device as defined in claim 4, further comprising means (25,26,27,28,29) for analyzing said sensor motion measurement signal and for signaling when said means for analyzing detects the presence of the irregular deflections.

7. The device as defined in claim 4, wherein said free end of said contact sensor (2) has a convex rounded off shape with a radius R equal to from half a width of said contact sensor (2) to 150 mm and an opposite end of the contact sensor (2) remote from the free end is held fixed by said mounting means.

8. The device as defined in claim 4, wherein said free end of said contact sensor (2) has a chamfered surface (6) on said free end and said chamfered surface is oriented at an acute angle $\beta$ equal to from 30 to 90° to the a plane passing through the contact sensor (2).

9. The device as defined in claim 4, wherein the means (4) for measuring the regular and the irregular deflections of the contact sensor is a vibration pickup.

10. The device as defined in claim 4, wherein the means (4) for measuring the regular and the irregular deflections of the contact sensor is an optical, magnetic, inductive or capacitive distance-measuring sensor.

11. The device as defined in claim 4, wherein the means (4) for measuring the regular and the irregular deflections of the contact sensor is an acoustical pickup.

* * * * *